United States Patent
Engelmayer et al.

(10) Patent No.: US 7,262,279 B2
(45) Date of Patent: Aug. 28, 2007

(54) LACTOFERRIN IN THE TREATMENT OF DIABETES MELLITUS

(75) Inventors: Jose Engelmayer, Houston, TX (US); Atul Varadhachary, Houston, TX (US)

(73) Assignee: Agennix, Inc., Houston, TX (US)

( * ) Notice: Subject to any disclaimer, the term of this patent is extended or adjusted under 35 U.S.C. 154(b) by 0 days.

(21) Appl. No.: 11/401,667

(22) Filed: Apr. 11, 2006

(65) Prior Publication Data

US 2006/0189513 A1   Aug. 24, 2006

Related U.S. Application Data

(62) Division of application No. 10/844,865, filed on May 13, 2004, now Pat. No. 7,034,126.

(60) Provisional application No. 60/470,549, filed on May 14, 2003.

(51) Int. Cl.
*A61K 38/40*   (2006.01)
*A61K 49/00*   (2006.01)

(52) U.S. Cl. .................. 530/400; 530/350; 530/395; 514/12; 514/8; 424/9.1; 424/85.1

(58) Field of Classification Search ............ 514/8, 514/6, 12; 530/350, 395, 400; 424/85.1, 424/9.1
See application file for complete search history.

(56) References Cited

U.S. PATENT DOCUMENTS 6,333,311 B1 * 12/2001 Nuijens et al. .............. 514/12

FOREIGN PATENT DOCUMENTS

WO   WO 01/72322   * 10/2001

OTHER PUBLICATIONS

Zagulski et al., Archivum Immunologiae et Therapiae Experimentalis 49, 431-438 (2001).*

* cited by examiner

*Primary Examiner*—Chih-Min Kam
(74) *Attorney, Agent, or Firm*—Fulbright & Jaworski LLP; Melissa Acosta

(57) ABSTRACT

The present invention relates to methods of using a composition of lactoferrin for the treatment of diabetes mellitus as manifested by a reduction in the levels of serum glucose, blood pressure, obesity, or glycosylated hemoglobin (HbA1c).

24 Claims, 4 Drawing Sheets

LACTOFERRIN IN THE TREATMENT OF DIABETES MELLITUS

CROSS-REFERENCE TO RELATED APPLICATIONS

This application is a divisional of 10/844,865 filed May 13, 2004, now U.S. Pat. No. 7,034,126, which claims the benefit of U.S. Provisional Application No. 60/470,549 filed May 14, 2003, which is incorporated herein by reference in its entirety.

TECHNICAL FIELD

The present invention relates to methods of using lactoferrin (LF) to reduce circulating glucose, in order to treat, prevent or reduce the incidence and severity of diabetes mellitus. More particularly, the present invention relates to methods of reducing circulating glucose levels by administering a composition of lactoferrin.

BACKGROUND OF THE INVENTION

Diabetes mellitus is a group of diseases characterized by high levels of blood glucose resulting from defects in insulin production, insulin action, or both. According to current estimates, 17 million people in the U.S., or approximately 6.2% of the population, have diabetes. Over 8% of adults (age 20 or older) have diabetes, while over 20% of Americans age 65 or older have the disease. Approximately 90-95% of all people diagnosed with diabetes have adult-onset, or Type 2 diabetes. The remaining 5-10% of people with diabetes (generally children and young adults) have insulin-dependent, or Type 1, diabetes. The risk of developing diabetes increases with age or obesity levels. One million new cases are diagnosed in adults each year. In 1999, approximately 450,000 deaths due to diabetes occurred among people 25 years or older. This figure represents about 19% of all deaths in this age group. Complications of diabetes include heart disease, stroke, high blood pressure, blindness, kidney disease, nervous system disease, amputations, dental disease, and complications during pregnancy.

In order to survive, people with Type 1 diabetes must have insulin delivered by a pump or injections. People with Type 2 diabetes may be able to control their blood glucose by following a careful diet and exercise program, losing excess weight, and/or taking oral medication. Many people with diabetes also need to take medications to control their cholesterol and blood pressure. Among adults with diagnosed diabetes, about 11% take both insulin and oral medications, 22% take insulin only, 49% take oral medications only, and 17% do not take either insulin or oral medications. Most non-insulin therapies are oral drugs designed to either lower blood glucose levels or improve the sensitivity of the body's insulin to varying glucose levels. Oral anti-diabetics account for about 63% of the total anti-diabetic drug sales. Glucophage (metformin) had been the leading product, and it works by keeping the liver from making too much sugar, but it does not work for everyone, and effectiveness typically decreases over time. A newer class of drugs, insulin-sensitizers, lowers insulin resistance to help a diabetic's declining levels of insulin work harder and go farther. Currently marketed insulin-sensitizers are the two glitazones, Actos® and Avandia®. These two insulin-sensitizers are designed to be used as monotherapy or in combination with other antidiabetic drugs. However, glitazones have been associated with liver toxicity and death, so physicians remain cautious about the use of these drugs. There is a vast clinical need for safer and more effective therapies to treat diabetes.

Lactoferrin is a single chain metal binding glycoprotein. Many cells types, such as monocytes, macrophages, lymphocytes, and brush-border cells, are known to have lactoferrin receptors. Lactoferrin is found mainly in external secretions of mucosal epithelia such as breast milk, saliva, tears, bile, and pancreatic fluid and has a wide array of functions related to host primary defense mechanisms. For example, lactoferrin has been reported to activate natural killer (NK) cells, induce colony stimulating activity, activate polymorphonuclear neutrophils (PMN), regulate granulopoeisis, enhance antibody-dependent cell cytotoxicity, stimulate lymphokine-activated killer (LAK) cell activity, and potentiate macrophage toxicity.

The present invention is the first to use a lactoferrin composition as a means of lowering glucose levels as a treatment for diabetes mellitus.

BRIEF SUMMARY OF THE INVENTION

The present invention is directed to a method for modulating blood levels of glucose and insulin. The method of treatment involves administration of a lactoferrin composition.

An embodiment of the present invention comprises a method of modulating diabetes mellitus comprising the step of administering to a subject an effective amount of a lactoferrin composition, wherein the amount of the lactoferrin composition modulates at least one symptom of diabetes mellitus. Diabetes mellitus is non-insulin dependent diabetes mellitus or insulin dependent diabetes mellitus. The symptoms of diabetes mellitus can be selected from the group consisting of obesity, hyperglycemia, and increased insulin levels. Blood glucose is monitored by the level of glycosylated hemoglobin (HbA1c).

It is envisioned that the lactoferrin composition modulates the levels of insulin and/or blood glucose in the subject. In specific embodiments, the lactoferrin composition increases the levels of insulin and/or decreases the levels of blood glucose in the subject.

In further embodiments, the lactoferrin composition reduces the blood pressure in a subject suffering from diabetes mellitus induced high blood pressure. Still further, the lactoferrin composition reduces total body weight.

In certain embodiments of the present invention, the lactoferrin composition, which is dispersed in a pharmaceutically acceptable carrier, comprises lactoferrin or N-terminal lactoferrin variant in which at least the N-terminal glycine residue is truncated or substituted. The lactoferrin is mammalian lactoferrin, more particularly; the lactoferrin is human or bovine. Yet further, the lactoferrin is recombinant lactoferrin. In specific embodiments, the N-terminal lactoferrin variant comprises at least 1% of the lactoferrin composition, at least 5% of the lactoferrin composition, at least 10% of the lactoferrin composition, at least 25% of the lactoferrin composition, at least 50% of the lactoferrin composition or any range in between.

The lactoferrin composition can be formulated to be administered orally. Such formulations can comprise delayed release formulation so that the release of the composition occurs in the small intestine and/or in the large intestine.

Yet further, the lactoferrin composition of the present invention can be administered parenterally, for example, intravenously or intramuscularly.

In still further embodiments, the lactoferrin composition can be administered topically, for example, subcutaneously or dermally.

The amount of the composition that can be administered is about 1 µg to about 20 g per day. More specifically, the amount of the composition that is administered is about 0.1 g to about 5 g per day.

In further embodiments, a metal chelator dispersed in a pharmaceutically acceptable carrier can also be administered with the lactoferrin composition. Preferred metal chelator include, but are not limited to ethylenediaminetetraacetic acid (EDTA) or [ethylenebis(oxyethylenenitrilo)] tetraacetic acid (EGTA). More preferably, the metal chelator is EDTA. The amount of EDTA that is administered is about 1 ng to about 1 g per day It is also further envisioned that the present method can be used in combination with an antidiabetic drug.

Another embodiment of the present invention is a method of treating a subject susceptible to diabetes mellitus comprising the step of administering to the subject an effective amount of a lactoferrin composition, wherein the amount reduces the incidence of diabetes mellitus.

Still further, another embodiment is a method of reducing blood glucose in a subject suffering from diabetes mellitus comprising the step of administering to the subject an effective amount of a lactoferrin composition, wherein the amount of the lactoferrin composition modulates blood glucose.

Another embodiment is a method of modulating blood insulin in a subject suffering from diabetes mellitus comprising the step of administering to the subject an effective amount of a lactoferrin composition, wherein the amount of the lactoferrin composition modulates blood insulin. Modulating blood insulin results in an increase in blood insulin and/or a decrease in blood insulin.

The foregoing has outlined rather broadly the features and technical advantages of the present invention in order that the detailed description of the invention that follows may be better understood. Additional features and advantages of the invention will be described hereinafter which form the subject of the claims of the invention. It should be appreciated that the conception and specific embodiment disclosed may be readily utilized as a basis for modifying or designing other structures for carrying out the same purposes of the present invention. It should also be realized that such equivalent constructions do not depart from the invention as set forth in the appended claims. The novel features which are believed to be characteristic of the invention, both as to its organization and method of operation, together with further objects and advantages will be better understood from the following description when considered in connection with the accompanying figures. It is to be expressly understood, however, that each of the figures is provided for the purpose of illustration and description only and is not intended as a definition of the limits of the present invention.

BRIEF DESCRIPTION OF THE DRAWINGS

For a more complete understanding of the present invention, reference is now made to the following descriptions taken in conjunction with the accompanying drawings.

DETAILED DESCRIPTION OF THE INVENTION

Figure 1:
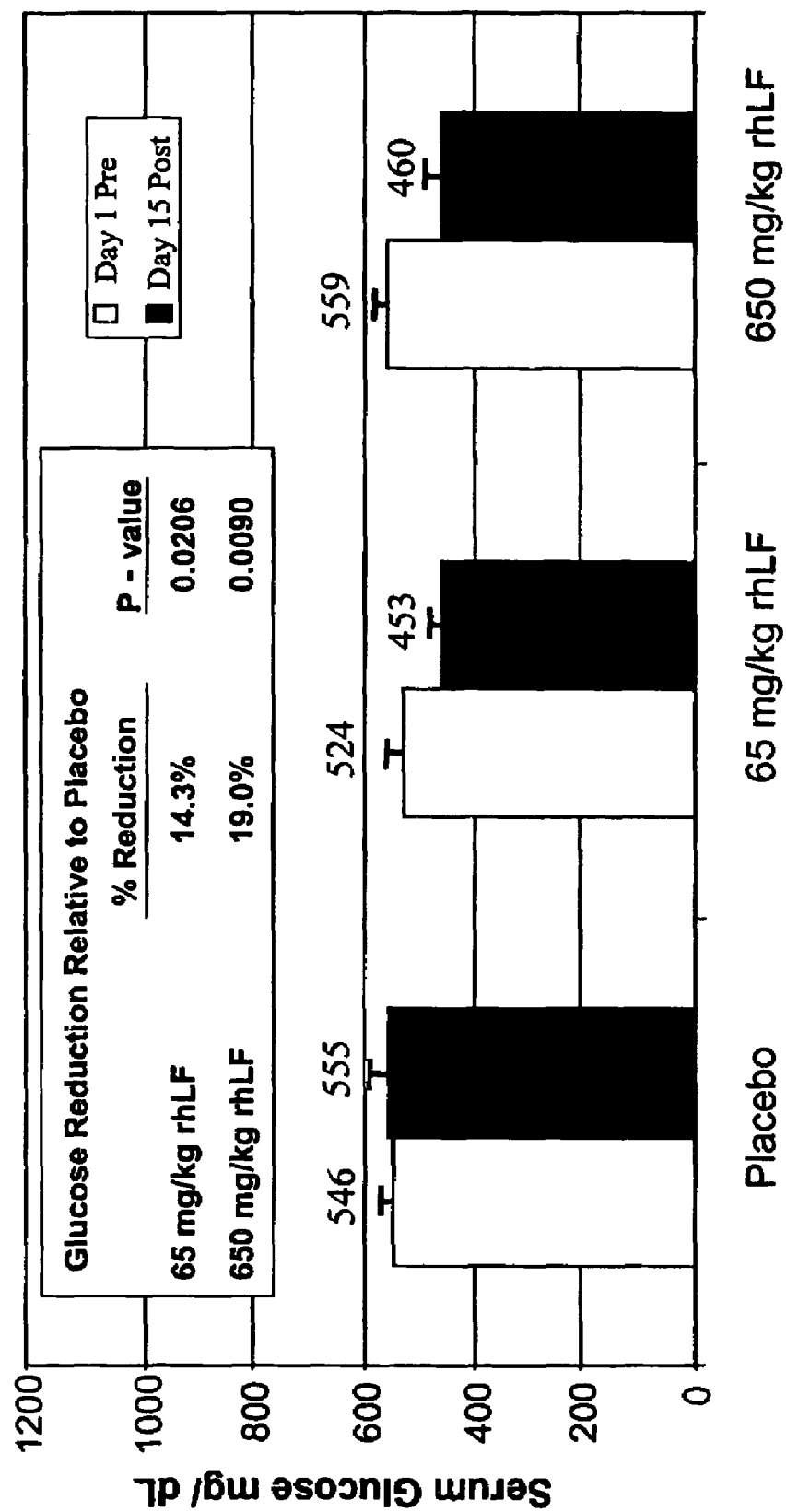
FIG. 1 shows the net reduction of blood glucose levels in mice receiving oral rhLF for fifteen days.

It is readily apparent to one skilled in the art that various embodiments and modifications can be made to the invention disclosed in this Application without departing from the scope and spirit of the invention.

A. Definitions

As used herein, the use of the word "a" or "an" when used in conjunction with the term "comprising" in the claims and/or the specification may mean "one," but it is also consistent with the meaning of "one or more," "at least one," and "one or more than one." Still further, the terms "having", "including" and "comprising" are interchangeable and one of skill in the art is cognizant that these terms are open ended terms.

The term "diabetes mellitus" as used herein refers to a disorder of carbohydrate metabolism that is typically characterized by hyperglycemia and glycosuria, which results from inadequate production or utilization of insulin. Diabetes mellitus includes several syndromes or disorders, for example, but not limited to, primary diabetes mellitus (e.g., insulin-dependent (Type I) and non-insulin-dependent (Type II)); secondary diabetes [for example: pancreatic diabetes (e.g., destruction of the pancreas, removal of the pancreas, etc.); extrapancreatic/endocrine diabetes (e.g., hypersomatotropism, hyperadrenalism, hyperthyroidism, glucagonama, etc.); drug-induced diabetes (e.g., steroid diabetes, thiazides, etc.)] and rare/exceptional forms of diabetes (e.g., lipoatrophic diabetes, myatonic diabetes, disturbance of insulin receptors, genetic syndromes, etc). Long-term complications of diabetes include neuropathy, retinopathy, nephropathy, generalized degenerative changes in the blood vessels and increased susceptibility to infection.

The terms "insulin-dependent diabetes mellitus"; "IDDM" or "Type I" refer to diabetes that is characterized by a hyperglycemia, glycosuria, and low blood insulin levels. Type I diabetes can develop at any age. It typically has an abrupt onset during the first two decades of life. Insulin therapy is usually required.

The term "lactoferrin" or "LF" as used herein refers to native or recombinant lactoferrin. Native lactoferrin can be obtained by purification from mammalian milk or colostrum or from other natural sources. Recombinant lactoferrin (rLF) can be made by recombinant expression or direct production in genetically altered animals, plants, fungi, bacteria, or other prokaryotic or eukaryotic species, or through chemical synthesis.

The term "lactoferrin composition" as used herein refers to a composition having lactoferrin, a portion or part of lactoferrin, an N-terminal lactoferrin variant, or a combination thereof.

The term "N-terminal lactoferrin variant" as used herein refers to lactoferrin wherein at least the N-terminal glycine has been truncated and/or substituted. N-terminal lactoferrin variants also include, but are not limited to deletion and/or substitution of one or more N-terminal amino acid residues, for example 1, 2, 3, 4, 5, 6, 7, 8, 9, 10, 11, 12, 13, 14, 15, or 16 N-terminal amino acid residues, etc. Thus, N-terminal lactoferrin variants comprise at least deletions or truncations and/or substitutions of 1 to 16 N-terminal amino acid residues. The deletion and/or substitution of at least the N-terminal glycine of lactoferrin mediates the same biological effects as full-length lactoferrin and/or may enhance lactoferrin's biological activity, for example by stimulating the production of various cytokines (e.g., IL-18, MIP-3α, GM-CSF or IFN-γ) by inhibiting various cytokines, (e.g., IL-2, IL-4, IL-5, IL-6, IL-10, and TNF-α) by improvement in the parameters relating to diabetes mellitus including blood levels of glucose or insulin (e.g., decreasing, reducing, inhibiting or abrogating high glucose, reducing total body weight, reducing glycosylated hemoglobin (HbA1c), reducing blood pressure or modulating blood insulin levels).

The terms "non-insulin-dependent diabetes mellitus"; "NIDDM" or Type II" refer to diabetes that is characterized by hyperglycemia and insulin levels being normal to high. Typically, Type II diabetes is a form of diabetes mellitus that has gradual onset in obese individuals over the age of 35. Insulin therapy is usually not required; however, Type II diabetes can be destined or prone to become fully insulin-dependent.

The term "metal chelator" as used herein refers to a compound which binds metal. Metal chelators that can be used in the present invention include the divalent metal chelators, for example, ethylenediaminetetraacetic acid (EDTA), [ethylenebis (oxyethylenenitrilo)] tetraacetic acid (EGTA), 1,2-bis(2-aminophenoxy)ethane-N,N,N',N'-tetraacetic acid (BAPTA), hydroxyethlene triamine diacetic acid, (HEDTA) or salts thereof.

The term "oral administration" as used herein includes oral, buccal, enteral or intragastric administration.

The term "parenteral administration" as used herein includes any form of administration in which the compound is absorbed into the subject without involving absorption via the intestines. Exemplary parenteral administrations that are used in the present invention include, but are not limited to intramuscular, intravenous, intraperitoneal, intraocular, or intraarticular administration.

The term "pharmaceutically acceptable carrier" as used herein includes any and all solvents, dispersion media, coatings, antibacterial and antifungal agents, isotonic and absorption delaying agents and the like. The use of such media and agents for pharmaceutically active substances is well known in the art. Except insofar as any conventional media or agent is incompatible with the vectors or cells of the present invention, its use in therapeutic compositions is contemplated. Supplementary active ingredients also can be incorporated into the compositions.

The term "subject" as used herein, is taken to mean any mammalian subject to which a human lactoferrin composition is administered according to the methods described herein. In a specific embodiment, the methods of the present invention are employed to treat a human subject. Another embodiment includes treating a human subject with elevated glucose levels according to the then medically established guidelines.

The term "therapeutically effective amount" as used herein refers to an amount that results in an improvement or remediation of the symptoms of the disease or condition.

The term "topical administration" as used herein includes dermal (e.g., trans-dermal or intra-dermal), epidermal, and subcutaneous.

The term "treating" and "treatment" as used herein refers to administering to a subject a therapeutically effective amount of a recombinant human lactoferrin composition so that the subject has an improvement in the parameters relating to diabetes mellitus including blood levels of glucose or insulin. The improvement is any observable or measurable improvement. Thus, one of skill in the art realizes that a treatment may improve the patient condition, but may not be a complete cure of the disease.

B. Lactoferrin

The lactoferrin used according to the present invention can be obtained through isolation and purification from natural sources, for example, but not limited to mammalian milk. The lactoferrin is preferably mammalian lactoferrin, such as bovine or human lactoferrin. In preferred embodiments, the lactoferrin is produced recombinantly using genetic engineering techniques well known and used in the art, such as recombinant expression or direct production in genetically altered animals, plants or eukaryotes, or chemical synthesis. See, e.g., U.S. Pat. Nos. 5,571,896; 5,571,697 and 5,571,691, which are herein incorporated by reference.

In certain aspects, the present invention provides lactoferrin variants having enhanced biological activities over natural LF and or rLF, e.g., the ability to stimulate and/or inhibit cytokines or chemokines. In particular, the invention provides variants of lactoferrin from which at least the N-terminal glycine residue has been substituted and/or truncated. The N-terminal lactoferrin variants may occur naturally or may be modified by the substitution or deletion of one or more amino acids.

The deletional variants can be produced by proteolysis of lactoferrin and/or expression of a polynucleotide encoding a truncated lactoferrin as described in U.S. Pat. No. 6,333,311, which is incorporated herein by reference.

Substitutional variants or replacement variants typically contain the exchange of one amino acid for another at one or more sites within the protein. Substitutions can be conservative, that is, one amino acid is replaced with one of similar shape and charge. Conservative substitutions are well known in the art and include, for example, the changes of: alanine to serine; arginine to lysine; asparagine to glutamine or histidine; aspartate to glutamate; cysteine to serine; glutamine to asparagine; glutamate to aspartate; glycine to proline; histidine to asparagine or glutamine; isoleucine to leucine or valine; leucine to valine or isoleucine; lysine to arginine; methionine to leucine or isoleucine; phenylalanine to tyrosine, leucine or methionine; serine to threonine; threonine to serine; tryptophan to tyrosine; tyrosine to tryptophan or phenylalanine; and valine to isoleucine or leucine.

In making such changes, the hydropathic index of amino acids may be considered. The importance of the hydropathic amino acid index in conferring interactive biologic function on a protein is generally understood in the art (Kyte and Doolittle, 1982). It is accepted that the relative hydropathic character of the amino acid contributes to the secondary structure of the resultant protein, which in turn defines the interaction of the protein with other molecules, for example, enzymes, substrates, receptors, DNA, antibodies, antigens, and the like.

Each amino acid has been assigned a hydropathic index on the basis of their hydrophobicity and charge characteristics (Kyte and Doolittle, 1982), these are: isoleucine (+4.5); valine (+4.2); leucine (+3.8); phenylalanine (+2.8); cysteine/cystine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5).

It is known in the art that certain amino acids may be substituted by other amino acids having a similar hydropathic index or score and still result in a protein with similar biological activity, e.g., still obtain a biological functionally equivalent protein. In making such changes, the substitution of amino acids whose hydropathic indices are within ±2 is preferred, those that are within ±1 are particularly preferred, and those within ±0.5 are even more particularly preferred.

It is also understood in the art that the substitution of like amino acids can be made effectively on the basis of hydrophilicity. U.S. Pat. No. 4,554,101, incorporated herein by reference, states that the greatest local average hydrophilicity of a protein, as governed by the hydrophilicity of its adjacent amino acids, correlates with a biological property of the protein. As detailed in U.S. Pat. No. 4,554,101, the following hydrophilicity values have been assigned to amino acid residues: arginine (+3.0); lysine (+3.0); aspartate (+3.0±1); glutamate (+3.0±1); serine (+0.3); asparagine (+0.2); glutamine (+0.2); glycine (0); threonine (−0.4); proline (−0.5±1); alanine (−0.5); histidine −0.5); cysteine (−1.0); methionine (−1.3); valine (−1.5); leucine (−1.8); isoleucine (−1.8); tyrosine (−2.3); phenylalanine (−2.5); tryptophan (−3.4).

Still further, it is understood that an amino acid can be substituted for another having a similar hydrophilicity value and still obtains a biologically equivalent and immunologically equivalent protein. In such changes, the substitution of amino acids whose hydrophilicity values are within ±2 is preferred, those that are within ±1 are particularly preferred, and those within ±0.5 are even more particularly preferred.

Thus, in the present invention, substitutional variants or replacement can be produced using standard mutagenesis techniques, for example, site-directed mutagenesis as disclosed in U.S. Pat. Nos. 5,220,007; 5,284,760; 5,354,670; 5,366,878; 5,389,514; 5,635,377; 5,789,166, and 6,333,311, which are incorporated herein by reference. It is envisioned that at least the N-terminal glycine amino acid residue can be replaced or substituted with any of the twenty natural occurring amino acids, for example a positively charged amino acid (arginine, lysine, or histidine), a neutral amino acid (alanine, asparagine, cysteine, glutamine, glycine, isoleucine, leucine, methionine, phenylaline, proline, serine, threonine, tryptophan, tyrosine, valine) and/or a negatively charged amino acid (aspartic acid or glutamic acid). Still further, it is contemplated that any amino acid residue within the range of N1 to N16 can be replaced or substituted. It is envisioned that at least up to 16 of the N-terminal amino acids residues can be replaced or substituted as long as the protein retains it biological and/or functional activity, which is stimulating the production of various cytokines (e.g., IL-18, MIP-3α, GM-CSF or IFN-γ), by inhibiting various cytokines, (e.g., IL-2, IL-4, IL-5, IL-6, IL-10, or TNF-α), and/or effecting parameters relating to diabetes mellitus including blood levels of glucose or insulin (e.g., decreasing, reducing, inhibiting or abrogating high glucose, reducing total body weight, reducing glycosylated hemoglobin (HbA1c), reducing blood pressure or modulating blood insulin levels). Thus, the N-terminal lactoferrin variants of the present invention are considered functional equivalents of lactoferrin.

In terms of functional equivalents, it is well understood by the skilled artisan that, inherent in the definition of a "biologically functional equivalent" protein is the concept that there is a limit to the number of changes that may be made within a defined portion of the molecule while retaining a molecule with an acceptable level of equivalent biological activity and/or enhancing the biological activity of the lactoferrin molecule. Biologically functional equivalents are thus defined herein as those proteins in which selected amino acids (or codons) may be substituted. Functional activity is defined as the ability of lactoferrin to stimulate or inhibit various cytokines or chemokines and/or effect parameters relating to diabetes mellitus including blood levels of glucose or insulin, for example decreasing, reducing, inhibiting or abrogating high glucose, reducing total body weight, reducing glycosylated hemoglobin (HbA1c), reducing blood pressure or modulating blood insulin levels.

Still further, the N-terminal amino acid residues can be substituted with a modified and/or unusual amino acids. A table of exemplary, but not limiting, modified and/or unusual amino acids is provided herein below.

TABLE 1

Modified and/or Unusual Amino Acids

| Abbr. | Amino Acid | Abbr. | Amino Acid |
| --- | --- | --- | --- |
| Aad | 2-Aminoadipic acid | EtAsn | N-Ethylasparagine |
| BAad | 3-Aminoadipic acid | Hyl | Hydroxylysine |
| BAla | beta-alanine, beta-Amino-propionic acid | AHyl | allo-Hydroxylysine |
| Abu | 2-Aminobutyric acid | 3Hyp | 3-Hydroxyproline |
| 4Abu | 4-Aminobutyric acid, piperidinic acid | 4Hyp | 4-Hydroxyproline |
| Acp | 6-Aminocaproic acid | Ide | Isodesmosine |
| Ahe | 2-Aminoheptanoic acid | Aile | allo-Isoleucine |
| Aib | 2-Aminoisobutyric acid | MeGly | N-Methylglycine, sarcosine |
| BAib | 3-Aminoisobutyric acid | MeIle | N-Methylisoleucine |
| Apm | 2-Aminopimelic acid | MeLys | 6-N-Methyllysine |
| Dbu | 2,4-Diaminobutyric acid | MeVal | N-Methylvaline |
| Des | Desmosine | Nva | Norvaline |
| Dpm | 2,2'-Diaminopimelic acid | Nle | Norleucine |
| Dpr | 2,3-Diaminopropionic acid | Orn | Ornithine |
| EtGly | N-Ethylglycine | | |

The presence and the relative proportion of an N-terminal lactoferrin variants (deletions and/or substitutions) in a preparation of lactoferrin (lactoferrin composition) may be done by determination of the N-terminal amino acid sequence by the process of Edman degradation using standard methods. A relative proportion of N-terminal lactoferrin variant comprises at least 1% of the lactoferrin composition, at least 5% of the lactoferrin composition, at least 10% of the lactoferrin composition, at least 25% of the lactoferrin composition, at least 50% of the lactoferrin composition or any range in between.

In this method, the protein is reacted with phenylisothiocyanate (PITC), which reacts with the amino acid residue at the amino terminus under basic conditions to form a phenylthiocarbamyl derivative (PTC-protein). Trifluoroacetic acid then cleaves off the first amino acid as its anilinothialinone derivative (ATZ-amino acid) and leaves the new amino terminus for the next degradation cycle.

The percentage of N-terminal lactoferrin variant may also be done more precisely by using a Dansylation reaction. Briefly, protein is dansylated using Dansyl chloride reacted with the protein in alkaline conditions (pH 10). Following the Dansylation, the reaction mixtures are dried to pellets, then completely hydrolyzed in 6N HCl. The proportion of N-terminal amino acids are identified by RP HPLC using an in-line fluorometer in comparison with standards made up of known dansylated amino acids.

C. Pharmaceutical Compositions

The present invention is drawn to a composition comprising a lactoferrin composition that is dispersed in a pharmaceutical carrier. The lactoferrin that is contained in the composition of the present invention comprises lactoferrin or an N-terminal lactoferrin variant in which at least the N-1 terminal glycine residue is truncated or substituted. More specifically, the N-terminal lactoferrin variant comprises at least 1% of the composition, at least 5% of the composition, at least 10% of the composition, at least 25% of the composition, at least 50% of the composition or any range in between.

Yet further, the composition comprises lactoferrin in combination with a metal chelator dispersed in a pharmaceutical carrier. Thus, the present invention is drawn to a lactoferrin composition with or without a metal chelator that is dispersed in a pharmaceutical carrier. One of skill in the art understands that both compositions (e.g., lactoferrin alone or lactoferrin in combination with a metal chelator) are within the scope of the present invention and can be used interchangeably depending upon the type of response that is desired. It is envisioned that the addition of a metal chelator to the lactoferrin composition enhances the sequestering of metal ions and thus strengthens the immune system or enhances the effect of lactoferrin.

Metal chelators that can be used in combination with lactoferrin, include the divalent metal chelators, for example, ethylenediaminetetraacetic acid (EDTA), [ethylenebis(oxyethylenenitrilo)] tetraacetic acid (EGTA), 1,2-bis(2-aminophenoxy)ethane-N,N,N',N'-tetraacetic acid (BAPTA), hydroxyethlene triamine diacetic acid, (HEDTA) or any salts thereof. More preferably, EDTA is used in combination with lactoferrin.

Administration of the lactoferrin compositions according to the present invention will be via any common route, orally, parenterally or topically. Exemplary routes include, but are not limited to oral, nasal, buccal, rectal, vaginal or topical, intradermal, transdermal, subcutaneous, intramuscular, intraperitoneal, intravenous, or intraarterial. Such compositions would normally be administered as pharmaceutically acceptable compositions as described herein.

Further in accordance with the present invention, the composition of the present invention suitable for administration is provided in a pharmaceutically acceptable carrier with or without an inert diluent. The carrier should be assimilable and includes liquid, semi-solid, e.g., pastes, or solid carriers. Except insofar as any conventional media, agent, diluent or carrier is detrimental to the recipient or to the therapeutic effectiveness of the composition contained therein, its use in administrable composition for use in practicing the methods of the present invention is appropriate. Examples of carriers or diluents include fats, oils, water, saline solutions, lipids, liposomes, resins, binders, fillers and the like, or combinations thereof.

In accordance with the present invention, the composition is combined with the carrier in any convenient and practical manner, e.g., by solution, suspension, emulsification, admixture, encapsulation, absorption and the like. Such procedures are routine for those skilled in the art.

In a specific embodiment of the present invention, the composition is combined or mixed thoroughly with a semi-solid or solid carrier. The mixing can be carried out in any convenient manner such as grinding. Stabilizing agents can be also added in the mixing process in order to protect the composition from loss of therapeutic activity, e.g., denaturation in the stomach. Examples of stabilizers for use in an the composition include buffers, amino acids such as glycine and lysine, carbohydrates such as dextrose, mannose, galactose, fructose, lactose, sucrose, maltose, sorbitol, mannitol, etc., proteolytic enzyme inhibitors, and the like. Yet further, it is envisioned that divalent metal chelators, for example EDTA, can also be used to stabilize the composition of the present invention. More preferably, for an orally administered composition, the stabilizer can also include antagonists to the secretion of stomach acids.

The composition for oral administration which is combined with a semi-solid or solid carrier can be further formulated into hard or soft shell gelatin capsules, tablets, or pills. More preferably, gelatin capsules, tablets, or pills are enterically coated. Enteric coatings prevent denaturation of the composition in the stomach or upper bowel where the pH is acidic. See, e.g., U.S. Pat. No. 5,629,001. Upon reaching the small intestines, the basic pH therein dissolves the coating and permits the lactoferrin composition to be released and absorbed by specialized cells, e.g., epithelial enterocytes and Peyer's patch M cells.

In another embodiment, a powdered composition is combined with a liquid carrier such as, e.g., water or a saline solution, with or without a stabilizing agent.

Further, the composition for topical administration which is combined with a semi-solid carrier can be further formulated into a gel ointment. A preferred carrier for the formation of a gel ointment is a gel polymer. Preferred polymers that are used to manufacture a gel composition of the present invention include, but are not limited to carbopol, carboxymethyl-cellulose, and pluronic polymers. Gel polymers prevent denaturation of the composition in the open skin by serum proteases.

The amount of lactoferrin in the present invention may vary from about 0.1 µg to about 100 g of lactoferrin per day. More preferably, lactoferrin is administered in the range of 1 µg to 20 g of lactoferrin per day. Yet further, in specific embodiments the amount of lactoferrin that is administered can be in the range of about 0.1 g to about 5 g. The lactoferrin may comprise lactoferrin or an N-terminal lactoferrin variant in which at least the N-1 terminal glycine residue is truncated and/or substituted.

More preferably, the composition of the present invention also contains metal chelators, for example, but not limited to ethylenediaminetetraacetic acid (EDTA), [ethylenebis (oxyethylenenitrilo)]tetraacetic acid (EGTA), 1,2-bis(2-aminophenoxy)ethane-N,N,N',N'-tetraacetic acid (BAPTA), hydroxyethlene triamine diacetic acid, (HEDTA) or salts thereof. The amount of the metal chelator in the composition may vary from about 1 ng to about 20 g. A preferred metal chelator is EDTA.

Upon formulation, solutions are administered in a manner compatible with the dosage formulation and in such amount as is therapeutically effective to result in an improvement or remediation of the symptoms. The formulations are easily administered in a variety of dosage forms such as ingestible solutions, drug release capsules and the like. Some variation in dosage can occur depending on the condition of the subject being treated. The person responsible for administration can, in any event, determine the appropriate dose for the individual subject. Moreover, for human administration, preparations meet sterility, general safety and purity standards as required by FDA Office of Biologics standards.

D. Treatment or Prophylaxis of Diabetes Mellitus

In accordance with the present invention, the composition provided in any of the above-described pharmaceutical carriers is administered to a subject who has experienced or is at high risk of having diabetes mellitus. Thus, it is envisioned that the lactoferrin composition of the present invention may be administered to a subject to regulate diabetes mellitus. The lactoferrin composition modulates at least one symptom of diabetes mellitus, for example, decrease blood glucose or modulate blood insulin levels.

Risk factors for type I diabetes include islet-cell antibodies and those of type 2 or gestational diabetes include inactivity, obesity, siblings with diabetes, and history of diabetes during pregnancy. One of skill in the art can determine the patients who would potentially benefit from a therapeutic agent that would reduce circulating levels of glucose. One of skill in the art can determine the therapeutically effective amount of the composition to be administered to a subject based upon several considerations, such as local effects, pharmacodynamics, absorption, metabolism, method of delivery, age, weight, disease severity and response to the therapy.

Oral administration of the composition includes oral, buccal, enteral or intragastric administration. It is also envisioned that the composition may be used as a food additive. For example, the composition is sprinkled on food or added to a liquid prior to ingestion.

In further embodiments, the composition is administered in conjunction with an antacid. Thus, an antacid is administered prior or substantially simultaneously with or after oral administration of the composition. The administration of an antacid just prior or immediately following the administration of the composition may help to reduce the degree of inactivation of the lactoferrin in the digestive tract. Examples of appropriate antacids include, but are not limited to, sodium bicarbonate, magnesium oxide, magnesium hydroxide, calcium carbonate, magnesium trisilicate, magnesium carbonate, and alumin hydroxide gel.

In addition to oral administration, the lactoferrin composition can also be administered parenterally (i.e., intramuscular, intraperitoneal, intravenous, intraarterial) or topically (i.e., intradermal, transdermal, or subcutaneous).

In a preferred embodiment of the present invention, the composition is administered in an effective amount to decrease, reduce, inhibit or abrogate high glucose, or to reduce total body weight, glycosylated hemoglobin (HbA1c), or blood pressure or to modulate blood insulin levels. In the case of a diabetic condition, successful reduction of hyperglycemia by the lactoferrin composition may be manifested by the fasting plasma glucose level falling below 126 mg/dL, the 2-hour plasma glucose level during an oral glucose tolerance test (OGTT) falling below below 200 mg/dL, or if a random plasma glucose determination reading below 200 mg/dL in a symptomatic individual. In the case of a pre-diabetic condition, a successful reduction of hyperglycemia by the lactoferrin composition may be manifested by the fasting plasma glucose falling below 110 mg/dL and/or the 2-hour plasma glucose on the OGTT falling below between 140 mg/dL. The amount of lactoferrin in the composition may vary from about 0.1 µg to about 100 g, more preferably, from about 1 µg to about 20 g, or any range therebetween. In specific embodiments, the composition that is administered contains the range of 0.1 g to 5 g of lactoferrin per day.

Glycohemoglobin (or glycosylated hemoglobin) is measured to monitor or accurately record blood glucose levels, and it is not influenced by acute changes in blood glucose or by the interval since the last meal. Glycohemoglobin is formed when glucose reacts non-enzymatically with the hemoglobin A molecule and is composed of several fractions, the major one being HbA1c. Total glycohemoglobin (HbA1) and HbA1c (expressed as the percentage of total hemoglobin) vary in proportion to the average level of glucose over the lifespan of the red blood cell (RBC), thereby providing an index of glycemic control.

Further aspects of the invention include reducing blood glucose in a patient suffering from diabetes mellitus by administering to a subject an effective amount of a lactoferrin composition such that the amount of the lactoferrin composition modulates blood glucose. The blood glucose is monitored by the level of glycosylated hemoglobin (HbA1c).

Another aspect is a method of modulating blood insulin in a patient suffering from diabetes mellitus by administering to a subject an effective amount of a lactoferrin composition such that the amount of the lactoferrin composition modulates blood insulin. Modulating blood insulin includes reducing or maintaining blood insulin levels or increasing blood insulin levels.

Modulating blood insulin levels in the present invention includes increasing blood insulin levels in insulin-dependent diabetes (Type I) or decreasing or maintaining insulin levels in non-insulin-dependent diabetes (Type II).

Treatment regimens may vary as well, and often depend on the health and age of the patient. Obviously, certain types of disease will require more aggressive treatment, while at the same time, certain patients cannot tolerate more taxing regimens. The clinician will be best suited to make such decisions based on the known efficacy and toxicity (if any) of the therapeutic formulations.

In specific embodiments, the composition is given in a single dose or multiple doses. The single dose may be administered daily, or multiple times a day, or multiple times a week, or monthly or multiple times a month. In a further embodiment, the lactoferrin is given in a series of doses. The series of doses may be administered daily, or multiple times a day, weekly, or multiple times a week, or monthly, or multiple times a month.

E. Combination Treatments

In order to increase the effectiveness of administration of the composition of the present invention, it is desirable to combine the lactoferrin compositions with an additional agent. For example, known diabetes agents are used in combination with the composition of the present invention. Exemplary agents known to treat high glucose or insulin sulfonylureas, biguanides, alpha-glucosidase, thiazolidinedione, meglitinide, and amino acid D-phenylalanine derivative. Other antidiabetic agents may also include, a weight loss regimen and/or a diet alteration.

The composition of the present invention may precede, be co-current with and/or follow the other agent(s) by intervals ranging from minutes to weeks. In embodiments where the composition of the present invention, and other agent(s) are applied separately to a cell, tissue or organism, one would generally ensure that a significant period of time did not expire between the time of each delivery, such that the composition and agent(s) would still be able to exert an advantageously combined effect on the cell, tissue or organism.

Various combination regimens of the composition and one or more agents are employed. One of skill in the art is aware that the composition of the present invention and agents can be administered in any order or combination.

F. Examples

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

Glucose Reduction by Recombinant Human Lactoferrin (rhLF) in Diabetic db/db Mice RhLF (650 mg/kg and 65 mg/kg) and vehicle/placebo (rhLF diluent buffer pH 7.0) were administered orally once daily for 15 consecutive days to groups of 4 non-insulin dependent diabetic mellitus (NIDDM) male mice. The NIDDM miceC57BLK/J-m+/Lepr db weighed approximately 60+5 grams, were 12 weeks of age and had a serum glucose of −560+mg/dl. All animals were allowed free access to normal laboratory chow and water. Blood samples were withdrawn from the orbital sinus immediately before dosing on day 1 (Day 1 Pre) and 90 minutes after the first administration on day 15 (Day 15 Post). The animals were fasted for 3 hours prior to sampling. Serum glucose levels were determined by enzymatic method (mutaratase-GOD). Four animals per cohort were studied. Reduction and p-value (1-tailed) were determined relative to placebo. As shown in FIG. 1, after 15 days of orally administering 65 mg/kg of RhLF there was a 14.6% reduction in serum glucose, while orally administering 650 mg/kg of RhLF resulted in a 19.0% reduction in serum glucose.

Example 2

Reduction of Insulin Levels by Recombinant Human Lactoferrin (rhLF)

Figure 2:
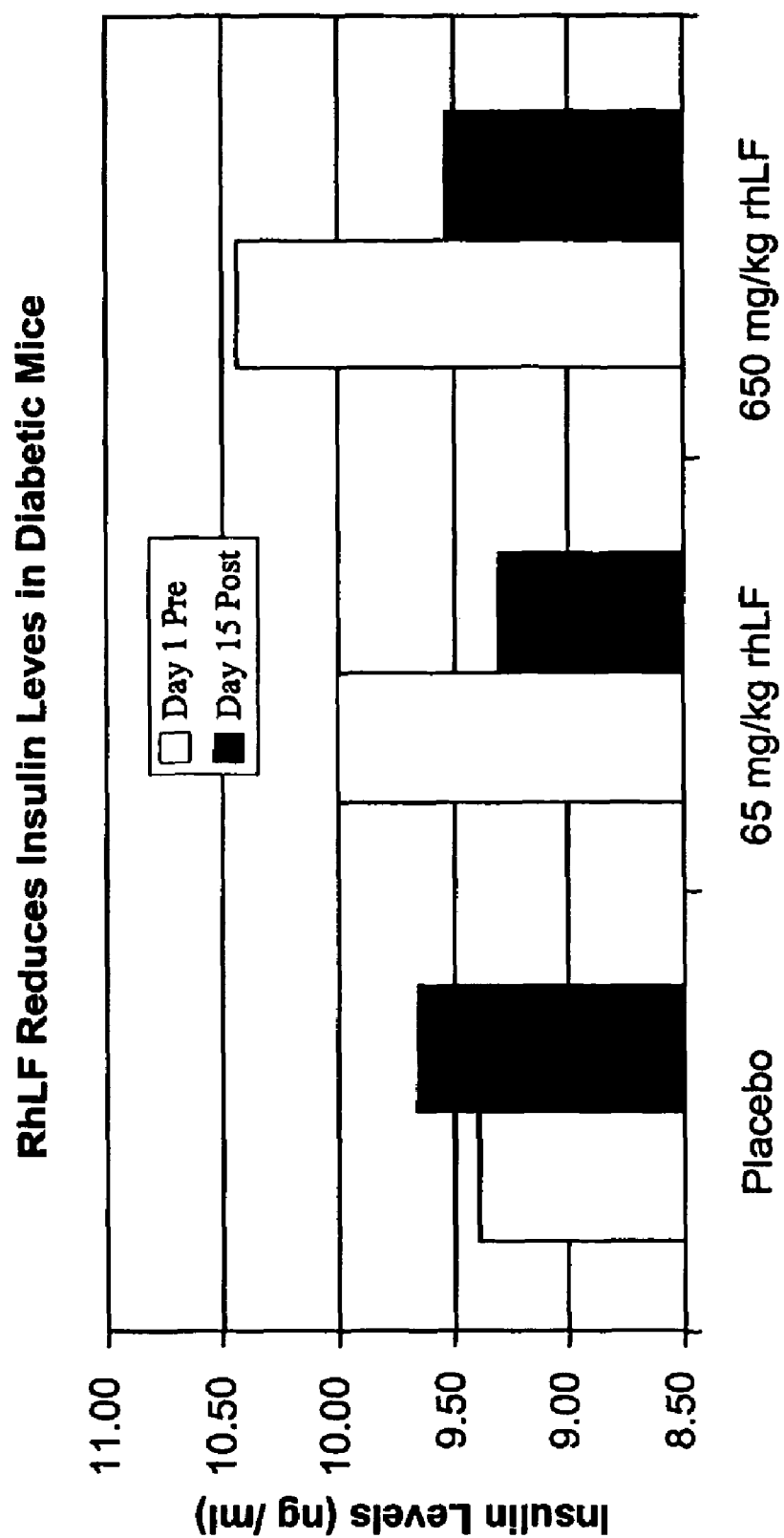
FIG. 2 shows the reduction of blood insulin levels in mice receiving oral rhLF for fifteen days.

RhLF (650 and 65 mg/kg) and vehicle/placebo (rhLF diluent buffer pH 7.0) were administered orally once daily for 15 consecutive days to groups of 4 non-insulin dependent diabetic mellitus (NIDDM) male mice. The NIDDM mice (C57BLK/J-m+/Lepr db) weighed approximately 60+5 grams, were 12 weeks of age, and had a serum glucose of −560+mg/dl). All animals were allowed free access to normal laboratory chow and water. Blood samples were withdrawn from the orbital sinus immediately before dosing on day 1 (Day 1 Pre) and 90 minutes after the last administration on day 15 (Day 15 Post). The animals were fasted for 3 hours prior to sampling. Serum insulin levels were determined by a specific ELISA assay as shown in FIG. 2, which illustrates that administration of RhLF resulted in an increase in serum insulin levels.

Example 3

Reduction of Glucose and Weight Levels in Diabetic Mice by RhLF

Figure 3:
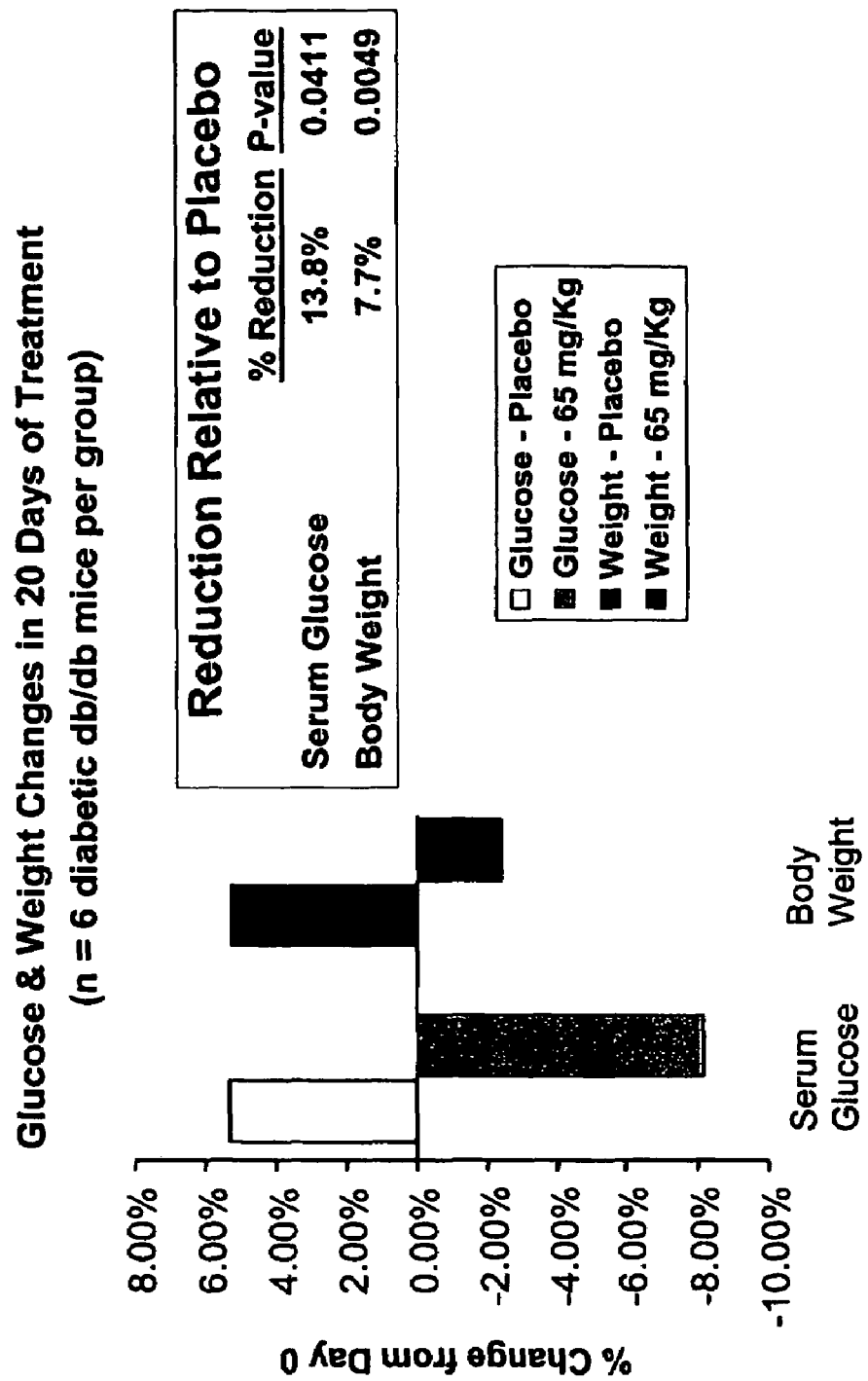
FIG. 3 shows the reduction of blood glucose levels and total body weight in mice receiving oral rhLF for twenty days.

Five groups of 6 non-insulin dependent diabetic mellitus (NIDDM) male mice (C57BLKS/J-m+/+Lepr db) weighing 50±grams and 9-10 weeks old were given either rhLF vehicle (Placebo), or RhLF (65 mg/kg) orally via gavage for 20 days (once per day) in a volume of 0.13 ml. Blood samples were obtained from the orbital sinus on day 0 and day 20 at 90 minutes following the last administration. Animals were fasted for 3 hours prior to sampling. Serum glucose levels were determined by enzymatic method (mutaratase-GOD). Total body weight measurements were determined on days 0 and 20. Percentage differences were determined with respect to pre-treatment values and analyzed statistically with the unpaired Student' t test. Differences were considered significant at p values of less than 0.05. FIG. 3 shows that following administration of RhLF there is a 13.8% reduction in serum glucose and 7.7% reduction in body weight.

Example 4

Dose Ranging Study of rhLF in the Reduction of Glucose and Insulin Levels in Diabetic Mice Diabetic mice with elevated levels of glucose or insulin are given orally placebo or ascending doses of rhLF for 15 days. Glucose and insulin levels are measured on day 0 and day 15.

Example 5

Study of rhLF in the Reduction of Glucose Levels in Type I Diabetic Mice

Type I or insulin-dependent diabetes mellitus (IDDM) is induced in mice by injection (55 mg/kg, IM) of streptozotocin in animals that are fasted 12 hours prior to treatment with lactoferrin. Alternatively, IDDM is induced in mice with intravenous streptozotocin (160 mg/kg). 48 hr later, RhLF (650 mg/kg and 65 mg/kg) and vehicle/placebo (rhLF diluent buffer pH 7.0) are administered orally or topically and are assessed for a reduction >20% of serum glucose. Treatment with insulin (s.c.) at 1 U/kg is used as a positive control.

Example 6

Dose Ranging Study of rhLF in the Reduction of Glucose Levels in Type I and Type II Diabetic Mice Mice with induced Type I or II diabetes with elevated levels of glucose are given a placebo or different doses of rhLF via different routes of administration. Glucose and insulin levels are measured on day 0, day 2, or day 15.

Example 7

Combination Therapy for Reduction of Glucose and Insulin Levels in Type I and Type II Diabetic Mice Type I or Type II Diabetic mice with elevated levels of glucose or insulin are given placebo, rhLF alone, or rhLF in combination with other drugs for 2-15 days. Glucose and insulin levels are measured on day 0, day 2, or day 15.

Example 8

Dose Ranging Study of RhLF in the Reduction of Glucose and Insulin Levels in Humans with Type I or Type II Diabetes Human patients with type I or type II diabetes and/or elevated levels of glucose or insulin are given oral or topical placebo or ascending doses of oral or topical rhLF for 30, 90 and 180 days. Glucose and insulin levels are measured as well as fluctuations in HbA1c.

Example 9

Combination Therapy for the Reduction of Glucose and Insulin Levels in Humans with Type I or Type II Diabetes Human patients with elevated levels of glucose or insulin are given oral or topical placebo, rhLF alone, or rhLF in combination with other drugs such as metformin (Glucophage) or any of the glitazones Actos and Avandia, for 30, 90 and 180 days. Glucose and insulin levels are measured as well as fluctuations in HbA1c.

Example 10

Reduction of Glucose Levels in Diabetic Mice by Topical RhLF

Figure 4:
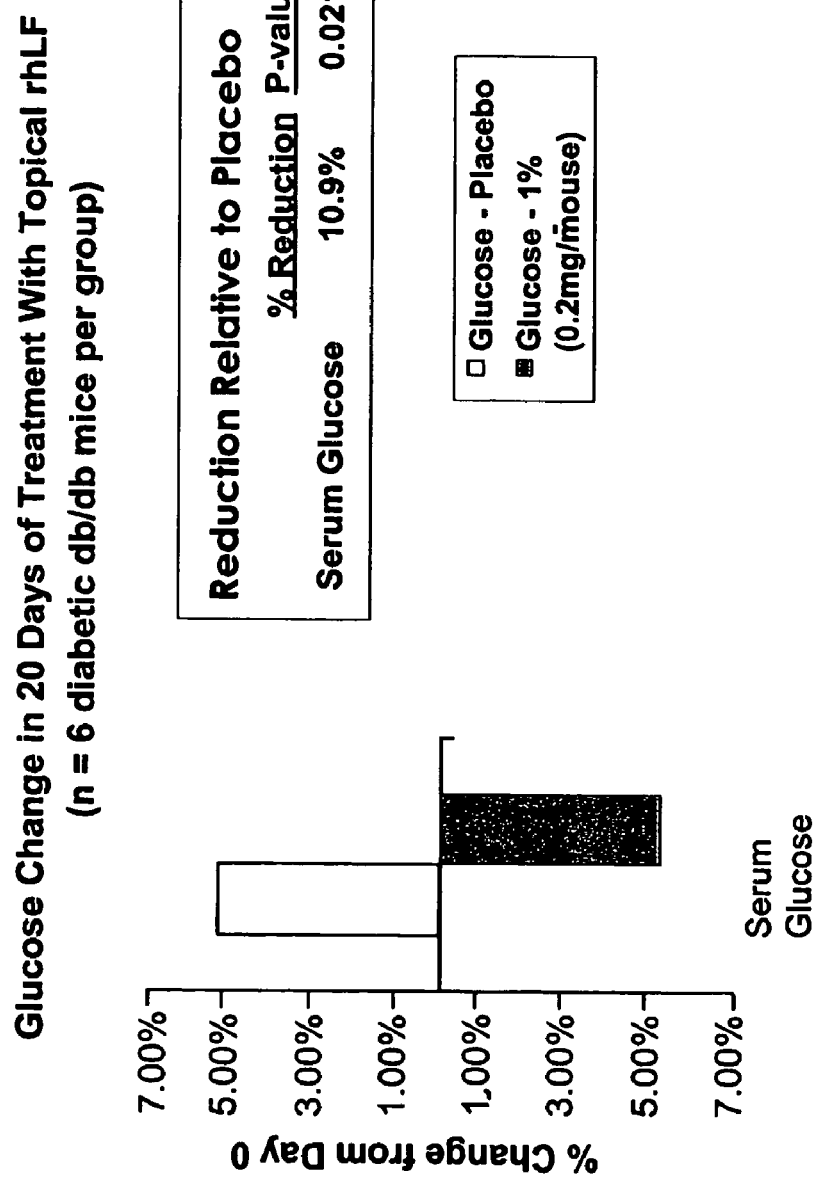
FIG. 4 shows the reduction of blood glucose levels in mice receiving topical rhLF for twenty days.

Two groups of 6 non-insulin dependent diabetic mellitus (NIDDM) male mice (C57BLKS/J-m+/+Lepr db) weighing 50+grams and 9-10 weeks old were given either rhLF vehicle (Placebo), or RhLF gel (1%) topically (0.2 mg per mouse/once per day) for 20 days applied directly onto a 12 mm punch excision. Blood samples were obtained from the orbital sinus on day 0 and day 20 at 90 minutes. The animals were fasted for 3 hours prior to sampling. Serum glucose levels were determined by enzymatic method (mutaratase-GOD). Percentage differences were determined with respect to pre-treatment values and analyzed statistically with the unpaired Student' t test. Differences were considered significant at p values of less than 0.05 (FIG. 4). FIG. 4 shows that topical administration of RhLF resulted in a 10.9% reduction of serum glucose.

REFERENCE CITED

All patents and publications mentioned in the specifications are indicative of the levels of those skilled in the art to which the invention pertains. All patents and publications are herein incorporated by reference to the same extent as if each individual publication was specifically and individually indicated to be incorporated by reference.

U.S. Pat. No. 4,554,101
U.S. Pat. No. 5,571,691
U.S. Pat. No. 5,571,697
U.S. Pat. No. 5,571,896
U.S. Pat. No. 5,629,001
U.S. Pat. No. 5,220,007
U.S. Pat. No. 5,284,760
U.S. Pat. No. 5,354,670
U.S. Pat. No. 5,366,878
U.S. Pat. No. 5,389,514
U.S. Pat. No. 5,635,377
U.S. Pat. No. 5,789,166
U.S. Pat. No. 5,629,001
U.S. Pat. No. 6,333,311

Although the present invention and its advantages have been described in detail, it should be understood that various changes, substitutions and alterations can be made herein without departing from the spirit and scope of the invention as defined by the appended description. Moreover, the scope of the present application is not intended to be limited to the particular embodiments of the process, machine, manufacture, composition of matter, means, methods and steps described in the specification. As one of ordinary skill in the art will readily appreciate from the disclosure of the present invention, processes, machines, manufacture, compositions of matter, means, methods, or steps, presently existing or later to be developed that perform substantially the same function or achieve substantially the same result as the corresponding embodiments described herein may be utilized according to the present invention. Accordingly, the appended descriptions are intended to include within their scope such processes, machines, manufacture, compositions of matter, means, methods, or steps.

What is claimed is:

1. A method of treating diabetes mellitus comprising administering to a subject an effective amount of a lactoferrin composition having an N-terminal lactoferrin variant in combination with an effective amount of an antidiabetic drug, wherein the N-terminal lactoferrin variant retains the biological activity of full length lactoferrin, and wherein the effective amount of said lactoferrin composition and the effective amount of said antidiabetic drug decrease blood levels of glucose and insulin thereby treating diabetes mellitus.

2. The method of claim 1, wherein said N-terminal lactoferrin variant is mammalian lactoferrin.

3. The method of claim 1, wherein said N-terminal lactoferrin variant is human or bovine lactoferrin.

4. The method of claim 1, wherein said N-terminal lactoferrin variant is recombinant lactoferrin.

5. The method of claim 1, wherein the N-terminal lactoferrin variant lacks at least the N-terminal glycine residue.

6. The method of claim 1, wherein said N-terminal lactoferrin variant comprises at least 1% to at least 50% w/w of the lactoferrin composition.

7. The method of claim 1, wherein said diabetes mellitus is non-insulin dependent diabetes mellitus.

8. The method of claim 1, wherein the blood pressure in said subject is reduced.

9. The method of claim 1, wherein total body weight of the subject is reduced.

10. The method of claim 1, wherein said blood glucose is monitored by the level of glycosylated hemoglobin (HbA1c).

11. The method of claim 1, wherein said composition is dispersed in a pharmaceutically acceptable carrier.

12. The method of claim 1, wherein said composition is administered orally.

13. The method of claim 12 further comprising administering the composition in a delayed release formulation.

14. The method of claim 13, wherein the N-terminal lactoferrin variant release occurs in the small intestine.

15. The method of claim 13, wherein the N-terminal lactoferrin variant release release occurs in the large intestine.

16. The method of claim 1, wherein said composition is administered parenterally.

17. The method of claim 16, wherein parenteral administration is intravenously or intramuscularly.

18. The method of claim 1, wherein said composition is administered topically.

19. The method of claim 18, wherein topical administration is subcutaneously or dermally.

20. The method of claim 1, wherein the amount of the composition that is administered is about 1 μg to about 20 g per day.

21. The method of claim 1, wherein the amount of the composition that is administered is about 0.1 g to about 5 g per day.

22. A method of treating hyperglycemia in a subject comprising administering to a subject an effective amount of a lactoferrin composition having an N-terminal lactoferrin variant, in combination with an effective amount of an antidiabetic drug, wherein the N-terminal lactoferrin variant retains the biological activity of full length lactoferrin, and wherein the effective amount of said lactoferrin composition and the effective amount of said antidiabetic drug decrease blood glucose.

23. The method of claim 22, wherein said blood glucose is monitored by the level of glycosylated hemoglobin (HbA1c).

24. The method of claim 22, wherein the subject suffers from diabetes mellitus.

* * * * *